United States Patent [19]

Hanzawa et al.

[11] 4,452,273
[45] Jun. 5, 1984

[54] APPARATUS FOR CONTROLLING DROP-WISE FLOW OF FLUID MATERIAL

[75] Inventors: Yoshiki Hanzawa; Takahiro Soma, both of Fujinomiya, Japan

[73] Assignee: Terumo Kabushiki Kaisha, Tokyo, Japan

[21] Appl. No.: 407,423

[22] Filed: Aug. 12, 1982

[30] Foreign Application Priority Data

Aug. 28, 1981 [JP] Japan ............................ 56-134938

[51] Int. Cl.$^3$ ............................................. F16K 31/40
[52] U.S. Cl. ..................................... 137/486; 604/253
[58] Field of Search .......................... 137/487.5, 486; 604/253, 251

[56] References Cited

U.S. PATENT DOCUMENTS

| | | | |
|---|---|---|---|
| 3,450,153 | 6/1969 | Hildebrandt et al. | 137/486 |
| 3,800,794 | 4/1974 | Georgi | 137/487.5 |
| 4,261,388 | 4/1981 | Shelton | 137/487.5 |

Primary Examiner—Martin P. Schwadron
Assistant Examiner—Mark Malkin
Attorney, Agent, or Firm—Frishauf, Holtz, Goodman & Woodward

[57] ABSTRACT

A flexible tube connected to a drop chamber is closed off by a clamping force applied by a pinch clamp. A cam which presses against the pinch clamp to initiate the drop-wise flow of a fluid forms an electrical contact with an extension of the clamp. Prior to the start of drop-wise feed when the cam and clamp are not in contact, the cam is driven toward the clamp at high speed until contact is made, at which point the drop-wise feed begins. At the instant of contact, a control signal is produced in response to which a speed change-over circuit is actuated to drive the cam at low speed, whereby control is executed in such a manner that the fluid drop rate gradually approaches a set drop rate at the low speed.

7 Claims, 4 Drawing Figures

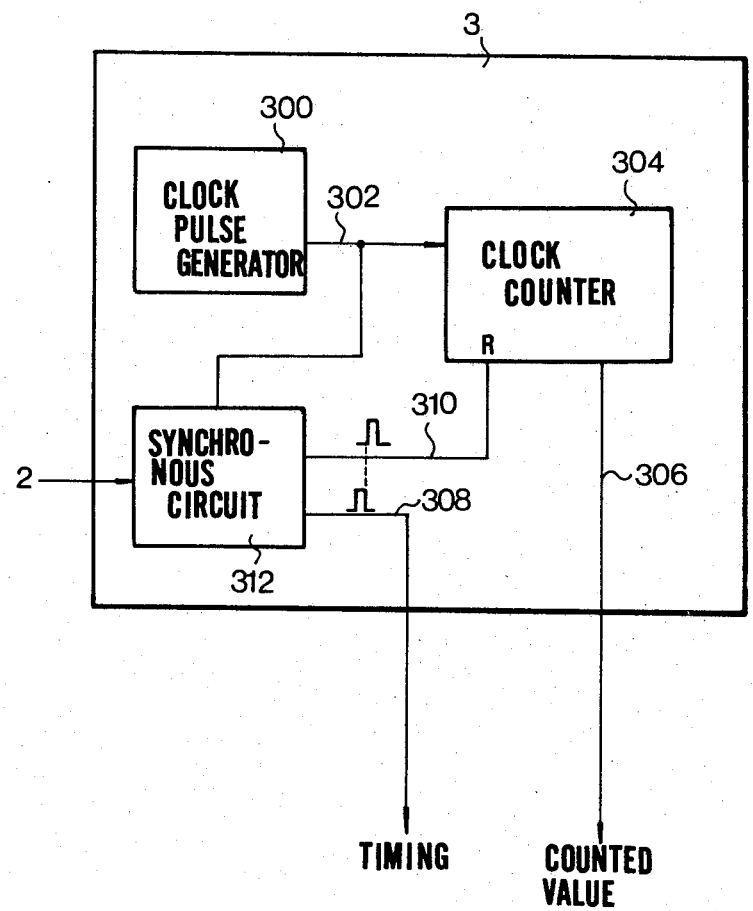

APPARATUS FOR CONTROLLING DROP-WISE FLOW OF FLUID MATERIAL

BACKGROUND OF THE INVENTION

1. Field of the Invention

This invention relates to an apparatus for controlling the drop-wise flow of a fluid material such as liquid medication, a physiological salt solution or blood, wherein the fluid flows in the form of free-falling drops under the influence of gravity. More particularly, the invention relates to improvements in an apparatus of the type described, in which the initial conditions for the control of the fluid drop-rate are established in a short period of time.

2. Description of the Prior Art

In intravenous feeding or blood transfusions it is necessary to maintain a preset drop-rate of fluid in a drop chamber. In order to control the fluid flow automatically, it is conventional practice to drive a pinch clamp by means of a cam coupled to a motor, whereby the diameter of the tubing connected to the drop chamber is adjusted to set the desired drop-rate. A factor which must be taken into consideration in the automatic clamping operation is a delay in the dropping of the fluid caused by the air pressure within the drop chamber and the resistance offered by the flow channel. The delay phenomenon causes the drop-wise feed of the fluid to lag behind the clamping action of the pinch clamp, and causes the feed rate control operation to start only after the pinch clamp has allowed the tube diameter to expand to an excessive degree. This results in a drop-rate which is outside the appropriate limits, and makes it necessary to increase the clamping force to back up to the zero-set position where there is complete cut off of the flow passage. The only way to avoid this inconvience has been to pass the point of zero flow-rate, determined by the pinching action of the clamp, at an extremely slow speed. Moreover, the point of zero-flow rate, namely the desired initial condition from which control of the fluid flow starts, is not a constant value every time as it is decided by the wall thickness and flexibility of the tubing, which may differ from one apparatus to the next. Accordingly, it has heretofore taken an excessively long time to establish the initial clamping conditions of the pinch clamp.

SUMMARY OF THE INVENTION

Accordingly, a general object of the present invention is to eliminate the disadvantages encountered in the conventional drop rate control apparatus.

A more specific object of the present invention is to provide an apparatus for controlling the drop-wise flow of fluid, wherein the pinch clamp is set to the position of a desired drop-rate in a short period of time.

Another object of the present invention is to provide an apparatus for controlling the drop-wise flow of fluid, wherein the drop rate of the fluid can be increased gradually from zero to the desired rate to facilitate automatic control of the number of drops and to prevent the delivery of an excess amount of the fluid at the beginning of feed.

In accordance with the present invention, these and other objects are attained by providing, in an apparatus for controlling the drop-wise flow of a fluid in a medical set for transfusions and intravenous feeding having a drop chamber and a flexible tube communicating therewith, means embracing the drop chamber for converting the drop-rate condition into an electrical signal, a stationary member provided at a portion of the flexible tube, a movable member disposed to confront the stationary member through the intermediary of the flexible tube and mechanically biased toward the stationary member to press the flexible tube, adjusting means moving the movable member against the mechanical bias for adjusting the flow rate of the fluid through the flexible tube, driving means for driving the adjusting means, control signal generating means, having the adjusting means and the movable member, for generating a control signal in response to contact between the adjusting means and movable member when the driving means brings the adjusting member into contact with the movable member from the non-contacting state, speed changeover means for changing over the driving means from a high-speed drive region to a low-speed drive region in response to the control signal, drop-rate setting means for setting a drop rate, and control means adapted to compare a signal produced by the drop-rate setting means and a signal produced by the converting means for moving the movable member, in the low-speed region, to a position relative to the stationary member which provides a drop rate equivalent to the set drop rate. In one aspect of the invention, the adjusting means is so controlled as to be out of contact with the movable member prior to the start of drop-wise flow so that the flexible tube is closed off by the movable member at such time.

In a modification of the invention, the drive means comprises a motor, the speed changeover means includes a first current supply loop and a second current supply loop, and the control signal, produced in response to the contact between the adjusting means and movable member of the control signal generating means, effects a changeover from the first current supply loop to the second current supply loop to drive the motor in the low-speed region. The speed changeover means is set so that a current which flows in the first current supply loop is greater than a current which flows in the second current supply loop. In another modification of the invention, the driving means includes a stepping motor, the speed changeover means includes a first pulse rate supply loop and a second pulse rate supply loop, and the control signal produced by the control signal generating means effects a changeover from the first pulse rate supply loop to the second pulse rate supply loop to drive the stepping motor in the low-speed region. The speed changeover means is set so that a pulse rate provided by the first pulse rate supply loop is greater than a pulse rate provided by the second pulse rate supply loop. The adjusting means may comprise a cam.

Further, the movable member employed in the preferred embodiment of the invention comprises an electrically conductive arm and the movable jaw of a pinch clamp. The electrical signal conversion means comprises a drop-rate sensing unit and a dropinterval measuring circuit. The drop-rate setting means includes a drop-rate setting unit and a time information generating circuit. The control means includes a time comparing circuit, a motor running time computing circuit or a pulse number computing circuit, a circuit for deciding the rotational direction of the motor, and a start/stop button.

Other features and advantages of the invention will be apparent from the following description taken in

BRIEF DESCRIPTION OF THE DRAWINGS

FIG. 4 is a block diagram of the drop interval time measuring circuit.

DESCRIPTION OF THE PREFERRED EMBODIMENT

Figure 1:
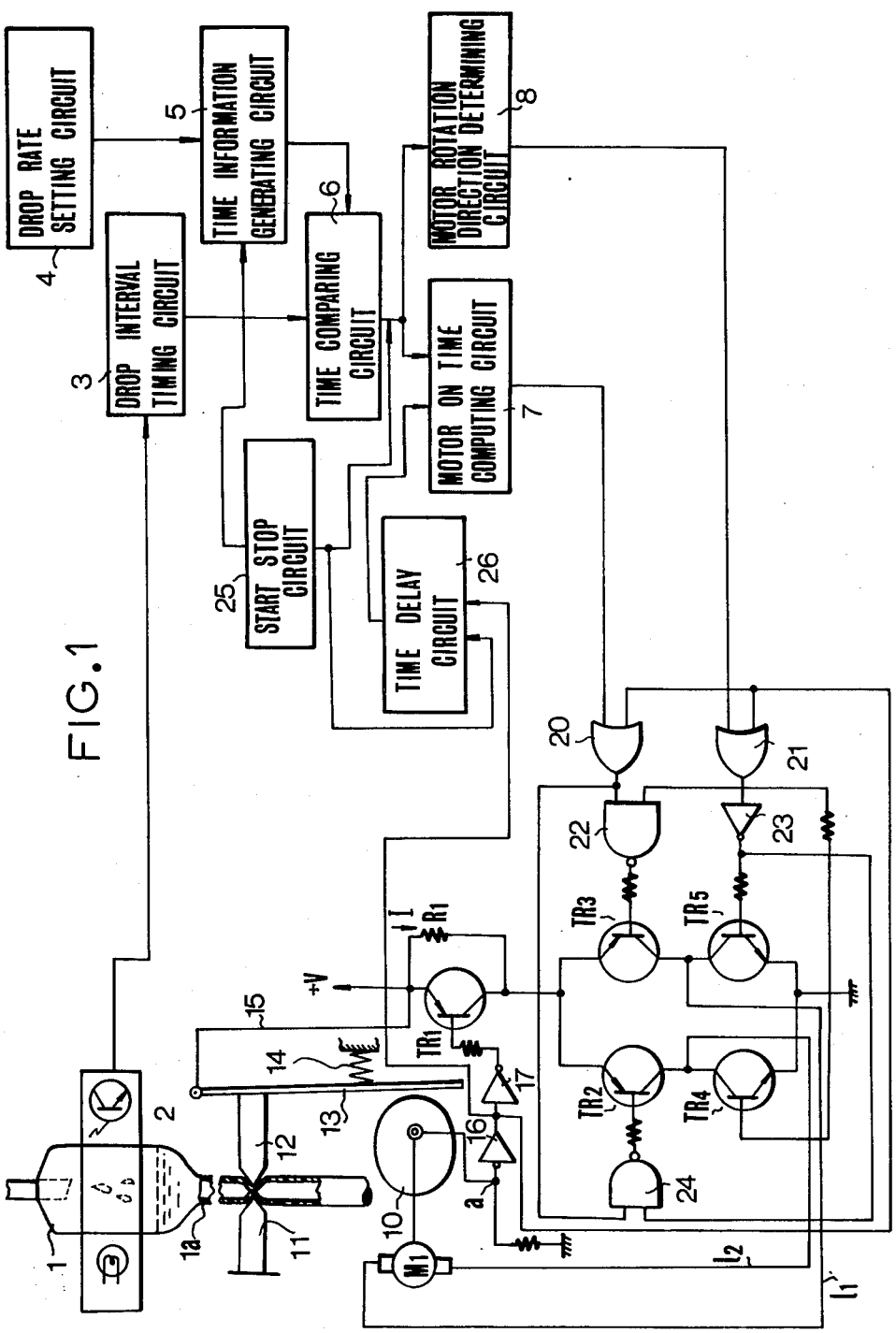
FIG. 1 is a system block diagram illustrating a preferred embodiment of the apparatus of the present invention.

In the embodiment of the invention as shown in FIG. 1, the drop-wise flow of a fluid supplied by fluid container (not shown) is sensed by means of a drop-sensing or pick-up unit 2 composed of a lamp and a light receptor, such as a phototransistor, disposed opposite each on either side of a drop chamber 1. The output of the drop-sensing unit 2, produced whenever a drop of fluid falls within the drop chamber, is applied to a measuring circuit 3 for measuring the time interval between drops. A rate setting unit 4 sets the desired drop rate, which is then converted into the time equivalent by a time information generating circuit 5. The time measured by the measuring circuit 3, and the time information generated by the time generating circuit 5, enter and are compared by a comparison circuit 6 whose output, based upon the result of the comparison operation, is connected to a circuit 7 for computing the running time of a motor, described later, and to a circuit 8 for determining the direction in which the motor is to rotate. The output of the running time computing circuit 7 is a signal having a time interval which in conformance with the magnitude of the signal input. The output of the direction determining circuit 8 is a binary signal which conforms to the polarity of the signal input.

The drop interval time measuring circuit 3 that receives the output of the drop sensing unit 2 can be constructed of well-known circuitry. For example, as shown in FIG. 4, the measuring circuit may include a clock pulse generator 300, a counter 304 for counting the generated clock pulses over an interval decided by the output of the drop sensing unit 2 and for delivering the counted value to the time comparing circuit 6, and means for determining the timing at which the counted value and the output of the time information generating circuit 5 are to be compared on the basis of the output from the drop sensing unit 2. A signal indicative of this timing is delivered to the time comparing circuit 6. The latter is operable to compare the output of the time measuring circuit 3, namely the output of the timer, against the time information provided by the time information generating circuit 5, which time information is a binary signal that corresponds to the value set by the drop-rate setting unit 4. Further, the timer has its output compared with the time information at a timing decided by the leading edge of the drop-sensor output, and is reset by a reset pulse produced in sync with the trailing edge of the drop-sensor output.

The drive means employed in this embodiment of the invention comprises a DC motor M1 whose rotational speed (r.p.m.) varies in accordance with a change in current commensurate with the magnitude of the applied voltage.

A flexible tube 1a is connected to the drop chamber 1 for leading the fulid to a hypodermic needle or a catheter, not shown. The flexible tube 1a is clamped by a pinch clamp comprising a stationary jaw 11 and a movable jaw 12 disposed opposite the stationary jaw 11 through the intermediary of the flexible tube 1a, thereby to enable pressing of the tube therebetween. The movable jaw 12 is provided on an electrically conductive arm 13 and forms a unitary body therewith. A cam 10, consisting of metal or of a material having an equivalent electrical conductivity, is rotated by the motor M1 through several stages of a reduction mechanism, not shown, and normally is not in contact with the conductive arm 13. An electrically insulating spring 14 is disposed between the arm 13 and a stationary portion of the apparatus and biases the arm 13, and hence the jaw 12, toward the flexible tube 1a. Thus the arm 13 causes the jaw 12 to clamp the flexible tube through the action of the spring 14 when the cam 10 is rotated to a position where it does not contact the arm 13. Speed changeover means comprising a driver circuit is provided for driving the motor M1 at high speed while there is no contact between the cam 10 and arm 13, and for driving the motor M1 at low speed when contact is established. Specifically, the speed changeover means comprises a parallel-connected resistor R1 and a PNP transistor TR1, the latter having its emitter connected to the power supply V1. The power supply V1 is connected also to the arm 13 via a wire lead 15. The cam 10 is connected to the base of the transistor TR1 through a pair of series-connected inverters 16, 17. When there is not contact between the cam 10 and arm 13, therefore, the transistor TR1 develops a low base-to-emitter potential, so that the transistor is driven into conduction, with the current from the power supply V1 flowing into the motor M1 through the low resistance path thus established. When the cam 10 comes into contact with the arm 13, on the other hand, the base of the transistor TR1 receives the same high potential as the emitter thereof. This causes the transistor to cut off, so that the power supply V1 is now connected to the motor M1 through the resistor R1.

Also provided is a polarity changeover circuit comprising four transistors TR2, TR3, TR4 and TR5. The emitters of transistors TR2 and TR3 are interconnected, as are the collectors of transistors TR2, TR4, the collectors of transistors TR3, TR5, and the emitters of transistors TR4, TR5. The emitters of transistors TR2, TR3 are further connected to the power supply V1, and the emitters of transistors TR4, TR5 to ground. One of the two power terminals of the motor M1 is connected to the common connection between the collectors of transistors TR2, TR4, and the other to the common connection between the collectors of transistors TR3, TR5.

An OR gate 20 receives the output of the motor running time computing circuit 7, as well as the output of inverter 16. Another OR gate 21 also receives the output of the inverter 16, as well as the output of the direction determining circuit 8. The outputs of OR gates 20, 21 are coupled to the base of transistor TR3 through a NAND gate 22. The output of OR gate 21 is also applied to the base of transistor TR5 through an inverter 23. The base of transistor TR2 receives, through a NAND gate 24, the output of OR gate 20 as well as the output of OR gate 21, inverted by the inverter 23.

Reference numeral 25 denotes a start/stop circuit which produces a high-level signal when a start button is depressed and which produces a low-level signal when a stop button is depressed. Reference numeral 26 denotes a time delay circuit. The time delay circuit 26 is energized when it receives the low-level signal from the start/stop circuit 25 and then receives a high-level signal from the inverter 16, further the output signal is delayed by a predetermined time interval e.g. 2 mm sec.

With respect to the correlation of the output of the start/stop circuit 25 and motor running time computing circuit 7, the circuit 7 acts so that it produces an output signal corresponding to the output value of circuit 6 while the output from the start/stop circuit 25 is at the high level. The motor rotation direction determining circuit 8 also produces the corresponding high- or low-level signal which is determined by the time comparing circuit 6 while the output of the start/stop circuit is at the high level. When the stop button is depressed and the circuit 25 produces the low-level signal, any output signal delivered from the time comparing circuit 6 is ignored in the motor rotation direction determining circuit 8, which produces an output signal that forcibly rotates the motor reversibly. When the low level output signal is delivered from the start/stop circuit 25 to the motor running time computing circuit 7, the input from the time comparing circuit 6 is inhibited and the output of the motor running time computing circuit 7, goes to the high level and then to the low level when the output of the delay goes high.

The delay circuit 26 delivers a high level signal, with a specified delay time, to the motor running time computing circuit 7 in order to halt the driving of the motor M1. A motor driving time for separating the cam from the arm by a distance of 2 mm is obtained by means of the delay circuit.

In operation, the control apparatus of the present invention is adapted to send a signal to the motor running time computing circuit 7 and direction determining circuit 8 when a transfusion or intravenous feeding operation ends. In response, the motor M1 is rotated in the reverse direction to separate the cam from the arm 13 by a distance of about two millimeters, whereby the jaw 12 on the arm is biased toward the stationary jaw 11 by the spring 14 to cut off the flow passage through the tube 1a. At the start of the next transfusion or intravenous feeding, at which time the the cam 10 and arm 13 will be in the non-contacting state, power is supplied to the apparatus by depressing a start/stop button 25 and a start signal is produced by the start/stop circuit 25 to initiate operation. Accordingly, the cam potential, connected to the input side of inverter 16 at point a, is low, so that the output of inverter 17 develops a low potential. Transistor TR1 therefore is driven into conduction. As a result, the power supply V1 is supplied, through line $1_1$, to one terminal of the motor M1 via transistor TR3 whose base is biased by a low potential. The other terminal of motor M1, connected to line $1_2$, is grounded through transistor TR4, rendered conductive by the output of OR gate 21. Thus a low-resistance path is constructed from power supply V1 to transistor TR4 through transistors TR1, TR3, line $1_1$, motor M1, and line $1_2$, in the order mentioned. Motor M1 therefore is rotated at high speed in the forward direction by a driving voltage substantially equal to that of the supply voltage V1. As a result, cam 10 makes contact with the arm 13, forming a closed circuit that connects the power supply V1 directly to the point a, raising it to a high potential that cuts off the transistor TR1. Since the outputs of circuits 7, 8 are high at this time, transistors TR3, TR4 are held in the conductive state, so that motor M1 continues to be rotated in the forward direction, but at a driving voltage which is now equivalent to V1–IR1. Owing to this diminished driving voltage, attributed to the resistance R1, the rotational speed of cam 10 is decelerated correspondingly, so that the arm 13 is deflected by the cam 10 at a speed reduced by the amount of deceleration. The movable jaw 12, moving away from the stationary jaw 11 at a slower rate in accordance with the travelling speed of the arm 13, increases the opening degree of the flexible tube 1a to deliver the fluid to the patient. As a result, there is a decline in the air pressure within the drop chamber 1, with the drop rate of the fluid becoming proportional to the movement of the jaw 12 after the lapse of a predetermined time delay. The drop sensing unit 2 senses the drop rate, which incorporates the above-described transient phenomena. When the comparator 6 finds that the sensed drop rate exceeds the value set by the rate setting unit 4, a signal is delivered to the direction determining circuit 8 whose output goes low as a result. In consequence, transistor TR5 conducts, transistor TR4 is cut off, and transistor TR2 is rendered conductive simultaneously. This causes a driving voltage of a reverse polarity (i.e., a polarity opposite to that of the driving voltage heretofore applied) to be impressed upon the motor M1 through a path consisting of the power supply V1, resistor R1, transistor TR2, line $1_2$, motor M1, line $1_1$, and transistor TR5, in the order mentioned. With the change in polarity, the motor is rotated reversely (opposite to the direction heretofore described) at the driving voltage equivalent to V1–IR1. As a result, the cam 10 is rotated gradually away from the arm 13 by the reversely rotating motor 10, whereby the spring 14 causes the arm 13 to move the jaw 12 toward the jaw 11 to restrict the diameter of the flexible tube 1a.

When the drop interval sensed by the sensing unit 2 coincides with the drop rate set by the rate setting unit 4 during execution of the foregoing operation, the time comparing circuit 6, upon detecting coincidence, sends a signal to the motor running time computing circuit 7 whose output signal goes low in response thereto. At this time the cam 10 will be in contact with arm 13 owing to the set conditions. Since transistors TR2 and TR3 will be non-conductive under these conditions, the supply voltage V1 is cut off from the motor M1, so that the apparatus executes drop-wise feed of the fluid at a steady drop rate set by the setting unit 4. In the event of a fluctuation in the drop rate caused by an external disturbance such as vibration or movement acting upon the tubing during the liquid feed, the above-described circuit operation will naturally cause the drop rate to follow and settle at the set rate. It also goes without saying that the drop rate setting unit 4, which sets the drop rate by means of a ten-key keyboard or digital switch, is capable of changing the drop rate even during the drop-wise feed of the fluid.

At the end of the fluid feed, as the low-level signal output is generated when the stop button is depressed, the current is supplied to the motor through the path V1, TR1, TR2, $1_2$, M1, $1_1$ and TR5, and it rotates the motor reversely.

When the cam separates from the arm, the high level signal goes to the delay circuit by the inverter.

When power is introduced by depressing the start/stop button 25, a reset operation takes place in which the time information generating circuit 5 as well as the counters and registers in the rest of the control circuitry are reset.

Figure 2:
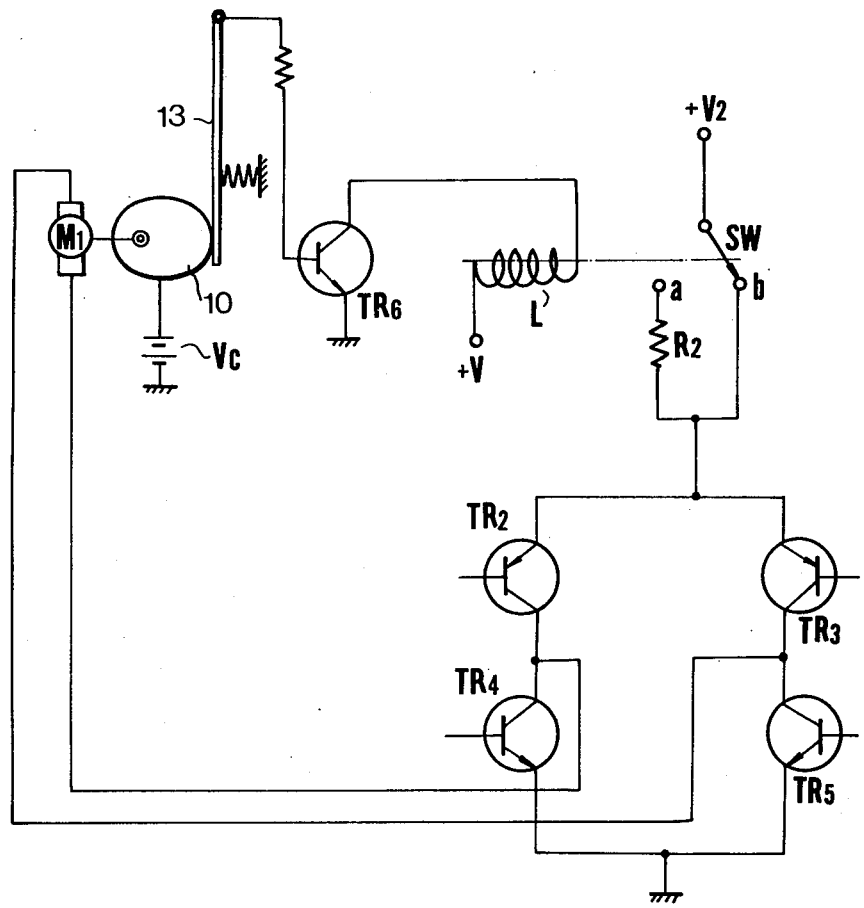
FIG. 2 is a block diagram illustrating a modification of the principal portion of the invention.

Various circuit arrangements can be devised for realizing the invention, one example of which is shown in FIG. 2. As shown, a transistor TR6 is provided and so connected as to be non-conductive when the cam 10 and arm 13 are not in contact. Specifically, the transistor TR6 has its base connected to the arm 13 through a resistor, its emitter connected to ground, and its collector connected to one end of a coil L whose other end is connected to +V. A switch SW actuated by the coil L has two switch positions a and b and connects a supply voltage of +V2 to the selected switch position. The cam 10 is connected to a control voltage Vc. When the cam 10 and arm 13 are not in contact, the switch SW is connected to side b since transistor TR6 is cut off, thereby driving the motor M1 at the supply voltage +V2. When the cam 10 is brought into contact with the arm 13 by the rotating motor, the base of transistor TR6 is connected to the control voltage Vc through the resistor, arm 13 and cam 10, thereby exciting the coil L. As a result, switch SW is changed over to side a to insert a resistor R2 between the voltage V2 and motor M1, which will be disposed in the polarity changeover circuitry. The motor M1 will thus be driven by a voltage lower than V2.

Figure 3:
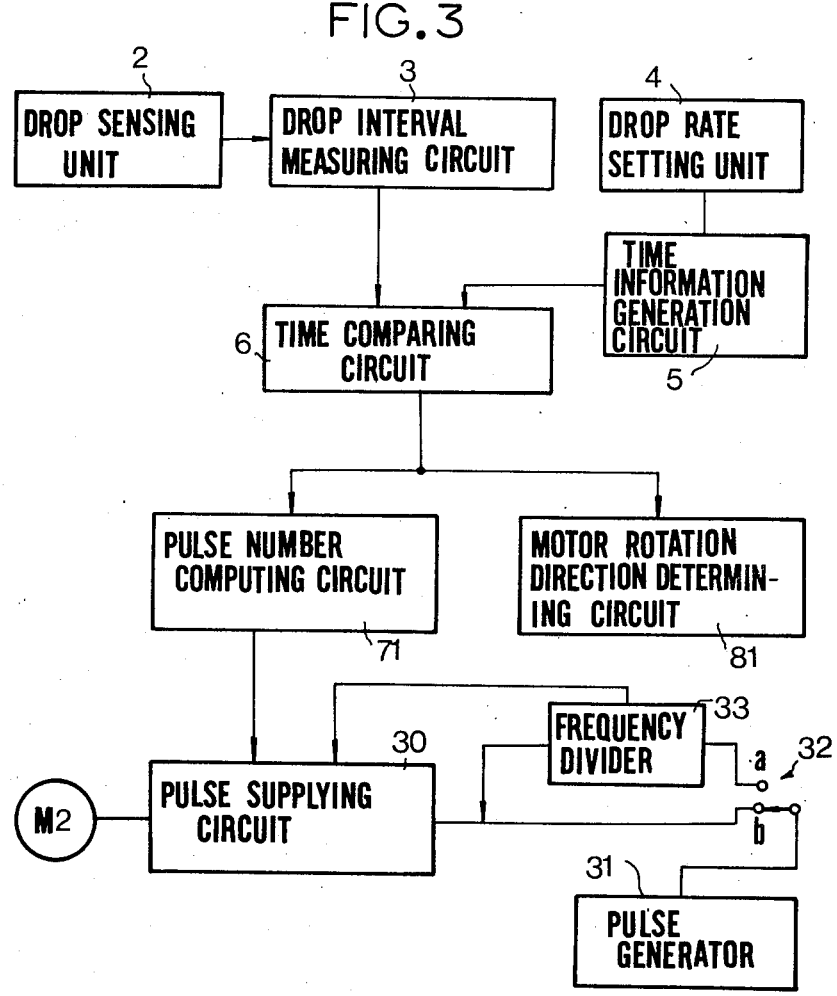
FIG. 3 is a block diagram illustrating another modification of the principal portion of the invention.

As shown in FIG. 3, a modification is possible wherein a stepping motor M2 is employed as the driving means. In brief, the dropping of the fluid, sensed by the drop sensing circuit 2, is converted into time by the drop interval measuring circuit 3. The time comparing circuit 6 compares the time from circuit 3 with the time (the output of the time generating circuit 5) corresponding to the drop-rate data set by the drop rate setting unit 4. The output of the comparator, based upon the result of the comparison operation, is connected to a pulse number computing circuit 71 and to a motor rotational direction dedetermining circuit 81. The optimum pulse number, based upon the valves being compared, is found from a read-only memory (ROM) which stores a reference table from which the number of driving pulses is read in response to the compared values. The pulse number computing circuit 71 receives pulses from a pulse generator 31 and provides a pulse supply circuit 30 with a number of pulses commensurate with the values being compared by the comparison circuit 6, the pulse supply circuit 30 driving the motor M2. The direction determining circuit 81 determines the direction in which the motor M2 is to rotate, based on the polarity of the output from the comparison circuit 6. Numeral 32 denotes an arrangement, as for example the one shown in FIG. 2, in which a switch having two sides a and b is actuated by a relay coil L to connect the output of the pulse generator 31 to the pulse supply circuit 30 directly or through a frequency divider 33.

In operation, the connection is to side b when the cam 10 and arm 13 are not in contact, so that the pulses generated by the pulse generator 31 are fed directly to the circuit 30 for driving the motor M2. The motor M2 therefore is supplied with pulses at a high rate f and rotated thereby at a high speed, so that the control apparatus is set to the initial condition in a short period of time. When the cam 10 makes contact with the arm 13, the transistor TR6 is rendered conductive to excite the coil L. The switch consequently is changed over to side a so that the pulses from the pulse generator 31 are applied to the frequency divider 33. As a result, the output pulses having the predetermined pulse rate f are divided by the dividing ratio N of the frequency divider, so that the stepping motor M2 now is driven by pulses at the lower pulse rate f/N. The stepping motor M2 therefore is reduced in speed, with the apparatus being so controlled as to execute drop-wise feed of the fluid at the predetermined drop rate. The actual control operation is similar to that described in connection with the embodiment illustrated in FIG. 1 and need not be described again here.

It should be noted that the drive means employed in the apparatus of the invention is not limited to the DC motor and stepping motor described in the foregoing embodiment. In other words, any motor that can be driven at high and low speeds and that is capable of rotating a cam reversibly can be used.

The actions and effects of the inventive apparatus, which is constructed and which operates in the manner described hereinabove, will now be set forth.

The apparatus includes means for converting the drop-rate condition into an electrical signal, a stationary member provided at one portion of the flexible tubing attached to the drop chamber, a movable member disposed to confront the stationary member and adapted to clamp the flexible tubing for regulating the flow rate of the fluid flowing therethrough, a cam for driving the movable member and driving means for rotating the cam, and speed changeover means for operating the driving means at a high speed until the cam, driven by the driving means, comes into contact with an extension of the movable member, and for operating the driving means at a low speed when the cam makes contact with the extension of the movable member. As a result, when the electrical contact between the cam and movable member is broken, the driving means operates in the high-speed region; when contact is made, the driving means operates in the low-speed region. The cam consequently is decelerated when contact is made and causes the movable member to clamp the flexible tubing at a slower speed, that is, at a speed reduced by the amount of cam deceleration.

Owing to the above-described operation, the drop-rate control apparatus is capable of arriving at the required initial conditions in a short period of time regardless of variances in flexible tube diameter. And, since the pinch clamp assembly is driven in very small increments as soon as the initial conditions are established, actual control of the drop rate can start with maximum compensation being made for the delay attributed to air pressure and flow passage resistance, and the fluid drop rate can be increased gradually from zero feed to the desired drop rate to facilitate automatic control of the drop rate and to prevent delivery of an excess amount of fluid at the beginning of feed. Furthermore, since the displacement detecting element for effecting control is realized directly by the movable member and driving means, control error and time delay can be minimized.

The apparatus of the invention further includes means for setting a predetermined drop rate, as well and control means for moving the movable member, at low speed, to the position that affords the predetermined drop rate upon comparing the output of the drop rate setting means and the output of the above-mentioned electrical signal conversion means. As a result, with the start of the drop-wise feed, the drop rate becomes proportional to the movement of the movable member, and the actual drop-rate condition is converted into an electrical signal by the conversion means. When the sensed drop rate is greater than the predetermined value set by the drop-rate setting means, the control means compares the signal produced by said setting means and the signal produced by the conversion means and then, based on the result of the comparison, moves the movable member, operating in the low-speed region, to the position that assures the predetermined drop rate. Thus the control means is operable to actuate the driving means in the reverse direction at low speed. In consequence, the cam is moved gradually away from the extension of the movable member, whereby the movable member, in constant pressing contact with the flexible tube, is moved in such a direction as will further constrict the diameter of the tube. When the drop interval sensed by the signal conversion means and the drop rate set by the setting means come into coincidence during the above-described operation, the action of the drive means is suspended by the control means to maintain the contact between the cam and the extension of the movable member, during which time the drop-wise feed of the fluid is executed at a rate in conformance with the predetermined rate set by the drop-rate setting means.

In accordance with the present invention, therefore, the drop rate centers on the set rate even if the drop rate is subjected to fluctuation during feed, as may be brought about by an external disturbance such as shaking or movement of the flexible tubing.

With a motor such as the DC motor serving as the driving means, the speed changeover means is provided with a driving circuit for operating the motor at high speed by supplying it with a large current when the contact formed by the cam and movable member is open, and at low speed by supplying it with a small current when the contact is closed. In such case the driving speed and direction of the motor are altered with facility, through a very simple construction.

With a motor such as the stepping motor serving as the driving means, the speed changeover circuit is provided with a driving circuit for operating the motor at high speed by supplying it with pulses at a high rate when the contact formed by the cam and movable member is open, and at low speed by supplying it with pulses at a low rate when the contact is closed. In this case the driving means can be controlled quantitatively in accordance with the difference between the set fluid drop rate and the actually measured fluid drop rate.

As many apparently widely different embodiments of the present invention can be made without departing from the spirit and scope thereof, it is to be understood that the invention is not limited to the specific embodiments thereof except as defined in the appended claims.

What we claim is:

1. An apparatus for controlling the drop-wise flow of a fluid in a medical set for transfusions and intravenous feeding having a drop chamber and a flexible tube communicating therewith, which apparatus comprises:
    means embracing the drop chamber for converting the drop-rate condition into an electrical signal;
    a stationary member provided at a portion of the flexible tube;
    a movable member disposed to confront said stationary member through the intermediary of the flexibe tube and mechanically biased toward said stationary member to press the flexible tube;
    adjusting means moving said movable member against the mechanical bias for adjusting the flow rate of the fluid through the flexible tube;
    driving means for driving said adjusting means;
    control signal generating means, having said adjusting means and said movable member, for generating a control signal in response to contact between said adjusting means and movable member when said driving means brings said adjusting member into contact with said movable member from the non-contacting state;
    speed changeover means for changing over said driving means from a high-speed drive region to a low-speed drive region in response to said control signal;
    drop-rate setting means for setting a drop rate; and
    control means adapted to compare a signal produced by said drop-rate setting means and a signal produced by said converting means for moving said movable member, in the low-speed region, to a position relative to said stationary member which provides a drop rate equivalent to the set drop rate.

2. Apparatus according to claim 1, in which said adjusting means is so controlled as to be out of contact with said movable member prior to the start of drop-wise flow so that the flexible tube is closed off by said movable member at such time.

3. Apparatus according to claim 1, in which said driving means comprises a motor, said speed changeover means includes a first current supply loop and a second current supply loop, and said control signal, produced in response to the contact between said adjusting means and movable member of said control signal generating means, effects a changeover from the first current supply loop to the second current supply loop to drive the motor in the low-speed region.

4. Apparatus according to claim 3, in which said speed changeover means is set so that a current which flows in said first current supply loop is greater than a current which flows in said second current supply loop.

5. Apparatus according to claim 1, in which said driving means comprises a stepping motor, said speed changeover means includes a first pulse rate supply loop and a second pulse rate supply loop, and said control signal produced by said control signal generating means effects a changeover from the first pulse rate supply loop to the second pulse rate supply loop to drive the stepping motor in the low-speed region.

6. Apparatus according to claim 5, in which said speed changeover means is set so that a pulse rate provided by said first pulse rate supply loop is greater than a pulse rate provided by said second pulse rate supply loop.

7. Apparatus according to claim 1, in which said adjusting means comprises a cam.

* * * * *